United States Patent [19]

Sheets et al.

[11] Patent Number: 4,464,398

[45] Date of Patent: Aug. 7, 1984

[54] GERMICIDE AND AN IMPROVED METHOD FOR KILLING BACTERIA, FUNGUS AND/OR VIRUSES

[75] Inventors: Richard D. Sheets; Donald R. Huffman, both of Huntington, Ind.

[73] Assignee: Huntington Laboratories, Inc., Huntington, Ind.

[21] Appl. No.: 291,984

[22] Filed: Aug. 11, 1981

[51] Int. Cl.$^3$ .............................................. A61K 31/14
[52] U.S. Cl. ................................................... 424/329
[58] Field of Search ......................................... 424/329

[56] References Cited

U.S. PATENT DOCUMENTS

| | | | |
|---|---|---|---|
| 3,646,147 | 2/1972 | Dadekian | 424/329 |
| 3,836,669 | 9/1974 | Dadkian | 424/329 |
| 4,165,375 | 8/1979 | Berger et al. | 424/329 |
| 4,320,147 | 3/1982 | Schaeufele | 424/329 |

FOREIGN PATENT DOCUMENTS 1221224 2/1971 United Kingdom .

OTHER PUBLICATIONS

Ditoro, *Soap/Cosmetics/Chemical Specialties*, pp. 34–35, May 1980.
Lonza, Product Information, Formulation 70-12, Lonza Inc., Fair Lawn, N.J., Nov. 1978.
"Lonza's Formulation 70-12" label (Exhibit F.).
"Lonza's Formulation 70-12", Technical Memorandum (Exhibit G.).
HI-TOR Germicidal Detergent Huntington Lab. Inc. (Exhibit H.).
Lonza Formulation R-82, Product Information (Exhibit I.).

*Primary Examiner*—Delbert R. Phillips
*Assistant Examiner*—F. T. Moezie
*Attorney, Agent, or Firm*—David A. Lundy

[57] ABSTRACT

An improved bactericide, fungicide and viricide comprising about three parts weight didecyl dimethyl ammonium chloride having the structural formula of:

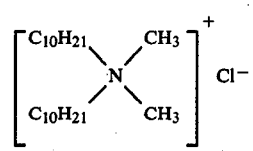

and about two parts weight of n-akyl (C14 50%, C12 40%, C16 10%) dimethyl ammonium chloride having the structural formula of:

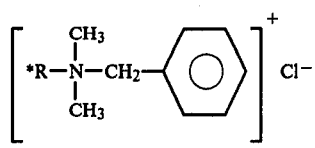

where R equals (C14 50%, C12 40%, C16 10%). In specific embodiments, the composition of the invention may include a non-ionic detergent, a detergent builder, diluents and/or other non-active ingredients. The method of the invention comprises bringing an inaminate article into contact with a solution of the improved germicidal composition of the invention in an appropriate use-dilution concentration. Totally surprising kills of bacteria, fungus and viruses when the improved germicidal composition is diluted with water, hard water, water in the presence of about 5% weight organic soil and hard water in the presence of 5% weight organic soil simultaneously.

18 Claims, No Drawings

GERMICIDE AND AN IMPROVED METHOD FOR KILLING BACTERIA, FUNGUS AND/OR VIRUSES

BACKGROUND OF THE INVENTION

The invention relates to an improved germicide and an improved method of killing bacteria, fungus and viruses using the improved germicide, and more particularly, to a germicide having surprising bacteriological activity and an improved method of killing bacteria, fungus and viruses which surprisingly is effective in the presence of water, water in the presence of 5% weight organic soil, hard water, and hard water in the presence of 5% weight organic soil simultaneously.

Germicidal compositions containing didecyl dimethyl ammonium chloride and quaternary ammonium chlorides have long been known. See U.S. Pat. No. 3,836,669 issued to Dadekian and initially assigned to Baird Chemical Industries, Inc. Also see U.S. Pat. No. 3,525,793 and U.S. Pat. No. 3,472,939 both issued to Petrocci et al. and initially assigned to Millmaster Onyx Corporation.

In the later 1960's and early 1970's, a germicide was formulated by Huntington Laboratories, Inc. containing the bacteriologically active compounds. See "New Generation Of Biologically Active Quaternaries", Richard D. Ditoro, CSMA, Proceedings of the 55th Annual Meeting, December, 1968. These germicidal compositions while known to be bacteriologically active gained only limited acceptance by the ultimate users such as hospitals, nursing homes and the like. In order to present to the hospital a germicidal compositions which when diluted for use had the clarity of water, a significant amount of ammonium sulphate had to be added to the composition. This ammonium sulphate caused the germicidal composition to "smell" of ammonia and have a noticeable smell long after the germicide was used. Both the ammonia smell and/or the possibility of a cloudy germicidal solution were unacceptable to the end users. By 1977 Huntington Laboratories, Inc. had ceased formulating its germicidal composition. Based upon this experience, it would be highly desirable to provide new and improved germicides which would have the same or similar bacteriological activity as these prior art germicides but without requiring ammonium sulphate to obtain water-clear solutions.

Additionally, upon the formation of governmental agencies having jurisdiction over germicidal compositions, governmental regulations and tests were formulated which had an impact upon the manufacturers of germicidal compositions. Currently, the Environmental Protection Agency of the United States Government requires manufacturers of germicidal compositions who claim disinfectant properties for its germicidal composition (i.e. that the composition kills microorganisms present except bacterial spores on inanimant surfaces), to establish kills when diluted to its published use-dilution with distilled water to qualify as a two step disinfectant, and such kills upon dilution with distilled water in the presence of five percent organic soil to qualify as a one step disinfectant. If a claim that a disinfectant can be used in hard water is made, then such kills must be established upon dilution with at least 400 ppm of synthetic hard water calculated as calcium carbonate. While some prior art compositions claim bacteriological effectiveness in hard water and some claim effectiveness in solutions containing 5% weight organic soil, such as blood serum, none of the prior art germicidal compositions known claim bacteriological effectiveness in hard water and in the presence of 5% weight organic soil simultaneously. Clearly, it is highly desirable to provide a new and improved germicidal compositions which can qualify as a disinfectant in hard water and in solutions containing 5% organic soil. It would further be desirable to provide improved germicidal compositions which can qualify as disinfectants in hard water and in the presence of 5% weight organic soil simultaneously. An improved germicidal composition making such a claim would indeed be a substantial advance in the art of germicidal compositions.

SUMMARY OF THE INVENTION

It is therefore a primary object of this invention to provide an improved germicidal composition.

It is another object of this invention to provide an improved germicidal composition which is an improved disinfectant.

It is another object of this invention to provide an improved germicidal composition which is both an improved disinfectant and a fungicide.

It is another object of this invention to provide an improved germicidal composition which is an improved disinfectant, a fungicide, and a viricide.

It is another object of this invention to provide an improved germicidal composition which is a disinfectant in solutions of both hard water and in the presence of 5% weight organic soil.

It is another object of this invention to provide an improved germicidal composition which is a disinfectant in solutions of hard water containing up to 400 parts per million calculated as calcium carbonate.

It is another object of this invention to provide an improved germicidal composition which is a disinfectant in the presence of 5% weight organic soil.

It is another object of this invention to provide an improved germicidal composition which is a disinfectant in solutions of hard water containing up to 400 parts per million calculated as calcium carbonate and in the presence of 5% weight organic soil.

It is finally an object of this invention to provide an improved germicidal composition which is a disinfectant, fungicide and viricide in solutions of hard water containing up to 400 parts per million calcium carbonate and in the presence of 5% weight organic soil simultaneously.

In the broader aspects of this invention there is provided an improved bactericide, fungicide and viricide comprising about three parts weight didecyl dimethyl ammonium chloride having the structural formula of:

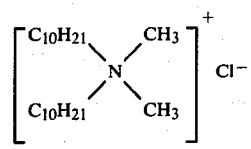

and about two parts weight of n-alkyl (C14 50%, C12 40%, C16 10%) dimethyl ammonium chloride having the structural formula of:

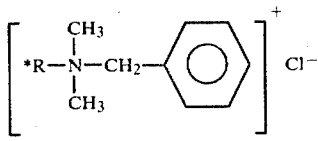

where R equals (C14 50%, C12 40%, C16 10%). In specific embodiments, the composition of the invention may include a non-ionic detergent, a detergent builder, diluents and/or other non-active ingredients. The method of the invention comprises bringing an inanimate article into contact with a solution of the improved germicidal composition of the invention in an appropriate use-dilution concentration. Totally surprising kills of bacteria, fungus and viruses when the improved germicidal composition is diluted with water, hard water, water in the presence of 5% weight organic soil and hard water in the presence of about 5% weight organic soil simultaneously.

DESCRIPTION OF A SPECIFIC EMBODIMENT

The improved germicidal compositions of the invention have exceptional bacteriological activity and an unusually high tolerance to hard water and to organic soil. Moreover, they have a sufficiently high tolerance to anionic surfactants to make them useful for sanitizing or disinfecting hard surfaces in the presence of anionic surfactants soaps and/or organic soil. Additionally, the improved germicidal compositions of the invention do not require any ammonium sulphate to render its solutions in distilled water or hard water or ordinary tap water "water clear"; and thus, do not posses any ammonia odor as did some prior art germicidal compositions. The improved compositions of the invention are particularly useful in laundry applications and as sanitizing and disinfecting compositions diluted in hard or soft water containing no organic soil or up to 5% weight organic soil. The improved compositions are particularly useful in sanitizing and disinfecting surfaces which have been previously cleaned with anionic detergents and contain residual amounts thereof with or without organic soil.

The germicidal compositions of the invention contain the quaternary ammonium compound didecyl dimethyl ammonium chloride having the structural formula of:

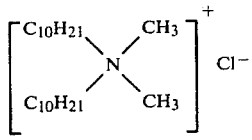

and the quaternary ammonium compound n-alkyl (C14 50%, C12 40%, C16 10%) dimethyl ammonium chloride having the structural formula of:

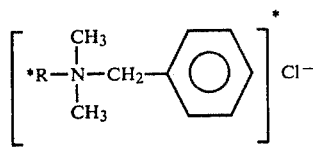

where R equals (C14 50%, C12 40%, and C16 10%) normal alkyl radicals.

Improved germicidal compositions may be formulated, in specific embodiments, with nonionic detergents and/or detergent builders. A typical formulation of a detergent disinfectant by weight is as follows:

| | |
|---|---|
| didecyl dimethyl ammonium chloride (50%) | 3 parts |
| n-alkyl (C14 50%, C12 40%, C16 10%) dimethyl benzyl ammonium chloride (50%) | 2 parts |
| linear primary ethoxylated alcohol | 1 part |
| tetrasodium ethylene diamine tetracetate (38%) | 1 part |
| water | 13 parts |

The anionic surfactants used for cleaning hard surfaces have a formula R-COOM, R-SO$_3$M or R-OSO$_3$M, where M represents an alkali metal, ammonium or substituted (amine) group and R represents an organic radical having more than 8 carbon atoms. Examples are soaps, fatty acid sarcosinates, alkyl sulfonates, alkyl sulfates, sulfated ethers of long chain aliphatic groups, sulfonated alkyl esters of long chain fatty acids, sulfonated glycol esters of long chain fatty acids, sulfonated alkyl substituted amides of long chain fatty acids, alkylated aryl sulfonates, alkyl sulfosuccinates, and organo phosphate ester surfactants. The definition of anionic surfactants also includes amphoteric surface active agents formulated at a pH above their isoelectric point. These ampholytic surfactants include N-fatty amino propionates, N-fatty iminodipropionates, cycloimidates and N-fatty aryl-N'-alkaline or amine carboxymethyl-N'-(2 hydroxy-ethyl) ethylene diamine.

The non-ionic surfactants which may be formulated with the quaternary compounds of the invention include:

(1) Monoethers of polyglycols with long-chain fatty alcohols, such as reaction products of ethylene oxide or polyethylene glycol with a long-chain fatty alcohol (e.g. reaction product of ethylene oxide and myristyl alcohol, viz:

$$C_{14}H_{29}(OC_2H_4)_nOH$$

where n is 5 to 20).

(2) Monoesters of polyglycols with long-chain fatty acids, such as reaction products of ethylene oxide or polyethylene glycol with a long-chain fatty acid (e.g. reaction product of ethylene oxide or polyethylene glycol with lauric acid, viz:

$$C_{11}H_{23}\overset{O}{\underset{\|}{C}}-(OCH_4)_nOH$$

where n is 5 to 20).

(3) Monoethers of polyglycols with alkylated phenols, such as reaction products of ethylene oxide or polyethylene glycol with an alkyl phenol (e.g. reaction product of ethylene oxide and nonyl phenol), viz:

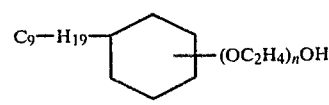

where n is 5 to 20.

(4) Polyoxyethylene sorbitan fatty and/or resin acid esters, e.g. polyoxyethylene sorbitan monolaurate. The latter is the reaction product of sorbitan monolaurate and either ethylene oxide or polyethylene glycol.

(5) N,N-polyethoxylates and polypropoxylates of long chain aliphatic amines. For example, the reaction product of either ethylene oxide or polyethylene glycol with coco amine yields:

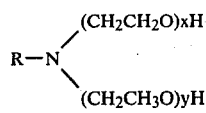

where R is coco and x+y=10 moles of ethylene oxide.

(6) N/N-polyethoxylates and/or polypropoxylates of long chain aliphatic acid amides. For example, the reaction product of either ethylene oxide or polyethylene glycol and hydrogenated tallow amide yields:

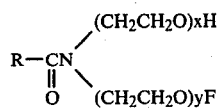

where RC is hydrogenated tallowamide x+y=50 moles of ethylene oxide.

The detergent builders which may be formulated with the quaternary compounds of the invention include:

(1) Water soluble inorganic alkaline builder salts alone or in admixture; e.g. carbonates, borates, phosphates, polyphosphates, bicarbonates and silicates. Specific examples of such salts are sodium tripolyphosphate, sodium carbonate, sodium tetraborate, sodium acid pyrophosphate, sodium bicarbonate, potassium tripolyphosphate, tetrapotassium pyrophosphate, sodium hexametaphosphate, sodium sesquicarbonate, trisodium phosphate, and potassium bicarbonate. Such inorganic builder salts enhance the detergency of the composition.

(2) Water soluble organic sequestrant builder salts used alone or in admixture, such as alkali metal, ammonium or substituted ammonium amino polycarboxylates, e.g., sodium and potassium ethylenediaminetetraacetate, sodium and potassium N-(2-hydroxyethyl) ethylenediaminetriacetates, sodium and potassium nitrilotriacetates and sodium potassium, and triethanolammonium N-(2-hydroxyethyl) iminodiacetates. Other organic sequestrant builder salts which can be used are: N-hydroxyethyliminodiacetates, dihydroxyethyl glycinates, diethylenetriamine-pentaacetates; 1,2-cyclohexanediamine tetraacetates. Mixed salts of these polycarboxylates are also suitable. Gluconic acid, phytic acid and their alkali and amine salts are also suitable as organic sequestrant builders.

In the case of laundry product applications, the compounds of the invention may be added during the washing or rinse cycle. When used during the wash cycle, they are fomulated with a non-ionic detergent so that the applied dose of is 50–3000 p.p.m. based on the dry weight of clothes load.

The improved germicidal compositions of the invention can also be used as a sanitizer. A typical formulation by weight is as follows:

| | |
|---|---|
| didecyl dimethyl ammonium chloride (50%) n-alkyl (C14 50%, C12 40%, C16 10%) | 0.75 parts |
| dimethyl benzyl ammonium chloride (50%) | 0.50 parts |
| linear primary ethoxylated alcohol | 0.25 parts |
| Tetrasodium ethylene diamine tetracetate | 0.25 parts |
| (38%) water | 81 parts |

If nonionic detergents and/or detergent builders are used in specific embodiments of the disinfectants and sanitizers of the invention, up to about 10 parts weight of a nonionic surfactant can be added for every 3 parts weight of didecyl dimethyl ammonium chloride plus 2 parts weight of n-alkyl (C14 50%, C12 40%, C16 10%) dimethyl benzyl ammonium chloride and up to about 10 parts weight of a detergent builder (20 parts weight total) can be added for every 3 parts weight of didecyl dimethyl ammonium chloride plus 2 parts weight of n-alkyl (C14 50%, C12 40%, C16 10%) dimethyl benzyl ammonium chloride.

It is widely known that it takes about 800 p.p.m. of n-alkyl (C14 50%, C12 40%, C16 10%) dimethyl benzyl ammonium chloride to kill Pseudomonas aeruginosa and approximately 500 p.p.m. of didecyl dimethyl ammonium chloride to kill Pseudomonas aeruginosa individually. Surprisingly, the improved germicidal compositions of this invention which contain a mixture of didecyl dimethyl ammonium chloride and n-alkyl (C14 50%, C12 40%, C16 10%) dimethyl benzyl ammonium chloride requires significantly smaller concentrations (only 488 p.p.m. of n-alkyl (C14 50%, C12 40%, C16 10%) dimethyl benzyl ammonium chloride and didecyl dimethyl ammonium chloride in a 40/60 ratio to kill Pseudomonas aeruginosa. Even further surprising is that Pseudomonas aeruginosa is killed by the improved germicidal compositions of this invention in solutions containing only 488 p.p.m. of n-alkyl (C14 50%, C12 40%, C16 10%) dimethyl benzyl ammonium chloride and didecyl dimethyl ammonium chloride in a 40 to 60 ratio in distilled water, in hard water, and in either distilled water or hard water in the presence of up to about 5% organic soil.

When the quaternary compounds of the invention are used for disinfecting their concentration in aqueous solutions range from about 200 to about 3000 ppm, preferable as dilutions range from about 300 to about 600 ppm. Similarly, when the quaternary compounds of the invention are for sanitizing their concentration in aqueous solutions range from about 50 to about 500 ppm, preferable use dilutions range from about 150 ppm to about 300 ppm.

The following examples are presented herein to more fully illustrate the present invention. While specific ingredients, ratios of ingredients, detergents, detergent builders, chelating agents, perfumes, diluents, and the like are used in these examples, it should be understood that the germicidal compositions of the invention can be formulated in a number of different ways and to include a number of different detergents, detergent builders, chelating agents, perfumes, diluents and the like. While the presence of n-alkyl (C14 50%, C12 40%, C16 10%) dimethyl benzyl ammonium chloride and didecyl dimethyl ammonium chloride is critical and essential to the performance of the germicidal compositions of the invention, a great variety of formulations containing these chlorides are useful and within the scope of this invention; it being well within persons skilled in the art to formulate other compositions or the invention in accordance with the disclosure herein.

EXAMPLE I 15 parts didecyl dimethyl ammonium chloride (50%), 10 parts n-alkyl (C14 50%, C12 40%, C16 10%) dimethyl benzyl ammonium chloride (50%), 5 parts linear primary ethoxylated alcohol, 4.33 parts tetrasodium ethylenediamine tetraacetate (38%), and 65.67 parts distilled water were all mixed together. The resulting mixture was then diluted with distilled water to include 488 p.p.m. n-akyl (C14 50%, C12 40%, C16 10%) dimethyl benzyl ammonium chloride and didecyl dimethyl ammonium chloride combined.

The bacteriological activity of the above formulation was illustrated by conducting Use-Dilution Confirmation Tests in accordance with the A.O.A.C. Manual, 12th Edition, 1975 pages 56-60. The following results were noted:

|  | No. of Carriers | No. of Positives |
|---|---|---|
| Gram-Negative Organisms |  |  |
| Pseudomonas aeruginosa | 90 | 0 |
| Salmonella choleraesuis | 90 | 0 |
| Enterobacter cloacae | 20 | 0 |
| Klebsiella pneumoniae | 20 | 0 |
| Proteus mirabilis | 20 | 0 |
| Shigella flexneri | 20 | 0 |
| Enterobacter aerogenes | 20 | 0 |
| Escherichia coli | 20 | 0 |
| Serratia marcescens | 20 | 0 |
| Proteus vulgaris | 20 | 0 |
| Shigella sonnei | 20 | 0 |
| Gram-Positive Organisms |  |  |
| Staphylococcus aureus | 180 | 0 |
| Staphylococcus aureus phage 80 | 60 | 0 |
| Staphylococcus aureus phage 81 | 60 | 0 |
| Streptococcus pyogenes | 20 | 0 |
| Staphylococcus epidermidis | 20 | 0 |

The fungicidal activity of the formulation was demonstrated according to the A.O.A.C. Fungicidal Test against Trychophyton interdigitale. See A.O.A.C. Fungicidal Test, 12th Edition, 1975, page 63. The following results were noted:

|  | 5 Minutes | | 10 Minutes | | 15 Minutes | |
|---|---|---|---|---|---|---|
|  | Prim. | Second. | Prim. | Second. | Prim. | Second. |
| Test I | — | — | — | — | — | — |
| Test II | — | — | — | — | — | — |

The formulation's activity as a viricide was also demonstrated according to viricidal carriers method accepted by the Environmental Protection Agency against Adenovirus Type III, Vaccinia, Influenza A/Texas, Herpes Virus Type I. The following results were noted:

EXAMPLE II 15 parts didecyl dimethyl ammonium chloride (50%), 10 parts n-alkyl (C14 50%, C12 40%, C16 10%) dimethyl benzyl ammonium chloride (50%), 5 parts linear primary ethoxylated alcohol, 4.33 parts tetrasodium ethylenediamine tetraacetate (38%), and 65.67 parts water were all mixed together. The resulting mixture was then diluted with water to include 488 p.p.m. n-alkyl (C14 50%, C12 40%, C16 10%) dimethyl benzyl ammonium chloride and didecyl dimethyl ammonium chloride combined. All water was hard water containing approximately 400 p.p.m. calculated as calcium carbonate.

The bacteriological activity of the above formulation was illustrated by conducting Use-Dilution Confirmation Tests, modified, in accordance with the A.O.A.C. Manual, 12th Edition, 1975 pages 56-60. The following results were noted:

|  | No. of Carriers | No. of Positives |
|---|---|---|
| Gram-Negative Organisms |  |  |
| Pseudomonas aeruginosa | 90 | 0 |
| Salmonella choleraesuis | 90 | 0 |
| Enterobacter cloacae | 20 | 0 |
| Klebsiella pneumoniae | 20 | 0 |
| Proteus mirabilis | 20 | 0 |
| Shigella flexneri | 20 | 0 |
| Enterobacter aerogenes | 20 | 0 |
| Escherichia coli | 20 | 0 |
| Serratia marcescens | 20 | 0 |
| Proteus vulgaris | 20 | 0 |
| Shigella sonnei | 20 | 0 |
| Gram-Positive Organisms |  |  |
| Staphylococcus aureus | 180 | 0 |
| Staphylococcus aureus phage 80 | 60 | 0 |
| Staphylococcus aureus phage 81 | 60 | 0 |
| Streptococcus pyogenes | 20 | 0 |
| Staphylococcus epidermidis | 20 | 0 |

The fungicidal activity of the formulation was demonstrated according to the A.O.A.C. Fungicidal Test, modified, against Trichophyton interdigitale. See A.O.A.C. Fungicidal Test, 12th Edition, 1975, page 63. The following results were noted:

|  | 5 Minutes | | 10 Minutes | | 15 Minutes | |
|---|---|---|---|---|---|---|
|  | Prim. | Second. | Prim. | Second. | Prim. | Second. |
| Test I | — | — | — | — | — | — |
| Test II | — | — | — | — | — | — |

The formulation's activity as a viricide was also demonstrated according to viricidal carriers method, modified, accepted by the Environmental Protection Agency against Adeno Virus Type III, Vaccinia, Influ-

|  | VIRUS: | $TCID_{50}$ | $TCLD_{50}$ | $TCTD_{50}$ | $TCID_{50} - TCLD_{50}$ |
|---|---|---|---|---|---|
| Test I | Adenovirus Type III | $1 \times 10^{-4.5/ml.}$ | $<1 \times 10^{-1/ml.}$ | $<1 \times 10^{-1/ml.}$ | $\geq 10^{4.5}$ log 10 |
| Test II | Adenovirus Type III | $1 \times 10^{-4.5/ml.}$ | $<1 \times 10^{-1/ml.}$ | $<1 \times 10^{-1/ml.}$ | $\geq 10^{4.5}$ log 10 |
| Test I | Vaccinia | $1 \times 10^{-5.5/ml.}$ | $<1 \times 10^{-1/ml.}$ | $<1 \times 10^{-1/ml.}$ | $\geq 10^{5.5}$ log 10 |
| Test II | Vaccinia | $1 \times 10^{-5.5/ml.}$ | $<1 \times 10^{-1/ml.}$ | $<1 \times 10^{-1/ml.}$ | $\geq 10^{5.5}$ log 10 |
| Test I | Influenza A/Texas | $1 \times 10^{-4.5/ml.}$ | $<1 \times 10^{-1/ml.}$ | $<1 \times 10^{-1/ml.}$ | $\geq 10^{4.5}$ log 10 |
| Test II | Influenza A/Texas | $1 \times 10^{-4.5/ml.}$ | $<1 \times 10^{-1/ml.}$ | $<1 \times 10^{-1/ml.}$ | $\geq 10^{4.5}$ log 10 |
| Test I | Herpesvirus Type I | $1 \times 10^{-4.3/ml.}$ | $<1 \times 10^{-1/ml.}$ | $<1 \times 10^{-1/ml.}$ | $\geq 10^{4.3}$ log 10 |
| Test II | Herpesvirus Type I | $1 \times 10^{-4.3/ml.}$ | $<1 \times 10^{-1/ml.}$ | $<1 \times 10^{-1/ml.}$ | $\geq 10^{4.3}$ log 10 | enza A/Texas, Herpes Virus Type I. The following were noted:

| VIRUS: | | $TCID_{50}$ | $TCLD_{50}$ | $TCTD_{50}$ | $TCID_{50} - TCLD_{50} =$ |
|---|---|---|---|---|---|
| Test I | Adenovirus Type III | $1 \times 10^{-4.5/ml.}$ | $<1 \times 10^{-1/ml.}$ | $<1 \times 10^{-1/ml.}$ | $\geq 10^{4.5}$ log 10 |
| Test II | Adenovirus Type III | $1 \times 10^{-4.5/ml.}$ | $<1 \times 10^{-1/ml}$ | $<1 \times 10^{-1/ml.}$ | $\geq 10^{4.5}$ log 10 |
| Test I | Vaccinia | $1 \times 10^{-5.5/ml.}$ | $<1 \times 10^{-1/ml.}$ | $<1 \times 10^{-1/ml.}$ | $\geq 10^{5.5}$ log 10 |
| Test II | Vaccinia | $1 \times 10^{-5.5/ml.}$ | $<1 \times 10^{-1/ml.}$ | $<1 \times 10^{-1/ml.}$ | $\geq 10^{5.5}$ log 10 |
| Test I | Influenza A/Texas | $1 \times 10^{-4.5/ml.}$ | $<1 \times 10^{-1/ml.}$ | $<1 \times 10^{-1/ml.}$ | $\geq 10^{4.5}$ log 10 |
| Test II | Influenza A/Texas | $1 \times 10^{-4.5/ml.}$ | $<1 \times 10^{-1/ml.}$ | $<1 \times 10^{-1/ml.}$ | $\geq 10^{4.5}$ log 10 |
| Test I | Herpesvirus Type I | $1 \times 10^{-4.3/ml.}$ | $<1 \times 10^{-1/ml.}$ | $<1 \times 10^{-1/ml.}$ | $\geq 10^{4.3}$ log 10 |
| Test II | Herpesvirus Type I | $1 \times 10^{-4.3/ml.}$ | $<1 \times 10^{-1/ml.}$ | $<1 \times 10^{-1/ml.}$ | $\geq 10^{4.3}$ log 10 |

EXAMPLE III 15 parts didecyl dimethyl ammonium chloride (50%), 10 parts n-alkyl (C14 50%, C12 40%, C16 10%) dimethyl benzyl ammonium chloride (50%), 5 parts linear primary ethoxylated alcohol, 4.33 parts tetrasodium ethylenediamine tetraacetate (38%), and 65.67 parts water were all mixed together. The resulting mixture was then diluted with distilled water to include 488 p.p.m. n-alkyl (C14 50%, C12 40%, C16 10%) dimethyl benzyl ammonium chloride and didecyl dimethyl ammonium chloride combined. All tests were conducted in the presence of 5% weight blood serum.

The bacteriological activity of the above formulation was illustrated by conducting Use-Dilution Confirmation Tests, modified, in accordance with the A.O.A.C. Manual, 12th Edition, 1975 pages 56-60. The following results were noted:

| | No. of Carriers | No. of Positives |
|---|---|---|
| Gram-Negative Organisms | | |
| Pseudomonas aeruginosa | 90 | 0 |
| Salmonella choleraesuis | 90 | 0 |
| Enterobacter cloacae | 20 | 0 |
| Klebsiella pneumoniae | 20 | 0 |
| Proteus mirabilis | 20 | 0 |
| Shigella flexneri | 20 | 0 |
| Enterobacter aerogenes | 20 | 0 |
| Escherichia coli | 20 | 0 |
| Serratia marcescens | 20 | 0 |
| Proteus vulgaris | 20 | 0 |
| Shigella sonnei | 20 | 0 |
| Gram-Positive Organisms | | |
| Staphylococcus aureus | 180 | 0 |
| Staphylococcus aureus phage 80 | 60 | 0 |
| Staphylococcus aureus phage 81 | 60 | 0 |
| Streptococcus pyogenes | 20 | 0 |
| Staphylococcus epidermidis | 20 | 0 |

The fungicidal activity of the formulation was demonstrated according to the A.O.A.C. Fungicidal Test, modified, against Trichophyton interdigitale. See A.O.A.C. Fungicidal Test, 12th Edition, 1975, page 63. The following results were noted:

| | 5 Minutes | | 10 Minutes | | 15 Minutes | |
|---|---|---|---|---|---|---|
| | Prim. | Second. | Prim. | Second. | Prim. | Second. |
| Test I | — | — | — | — | — | — |
| Test II | — | — | — | — | — | — |

The formulation's activity as a viricide was also demonstrated according to viricidal carriers method, modified, accepted by the Environmental Protection Agency against Adeno Virus Type III, Vaccinia, Influenza A/Texas, Herpes Virus Type I. The following results were noted:

| VIRUS: | | $TCID_{50}$ | $TCLD_{50}$ | $TCTD_{50}$ | $TCID_{50} - TCLD_{50} =$ |
|---|---|---|---|---|---|
| Test I | Adenovirus Type III | $1 \times 10^{-4.5/ml.}$ | $<1 \times 10^{-1/ml.}$ | $<1 \times 10^{-1/ml.}$ | $\geq 10^{4.5}$ log 10 |
| Test II | Adenovirus Type III | $1 \times 10^{-4.5/ml.}$ | $<1 \times 10^{-1/ml}$ | $<1 \times 10^{-1/ml.}$ | $\geq 10^{4.5}$ log 10 |
| Test I | Vaccinia | $1 \times 10^{-5.5/ml.}$ | $<1 \times 10^{-1/ml.}$ | $<1 \times 10^{-1/ml.}$ | $\geq 10^{5.5}$ log 10 |
| Test II | Vaccinia | $1 \times 10^{-5.5/ml.}$ | $<1 \times 10^{-1/ml.}$ | $<1 \times 10^{-1/ml.}$ | $\geq 10^{5.5}$ log 10 |
| Test I | Influenza A/Texas | $1 \times 10^{-4.5/ml.}$ | $<1 \times 10^{-1/ml.}$ | $<1 \times 10^{-1/ml.}$ | $\geq 10^{4.5}$ log 10 |
| Test II | Influenza A/Texas | $1 \times 10^{-4.5/ml.}$ | $<1 \times 10^{-1/ml.}$ | $<1 \times 10^{-1/ml.}$ | $\geq 10^{4.5}$ log 10 |
| Test I | Herpesvirus Type I | $1 \times 10^{-4.3/ml.}$ | $<1 \times 10^{-1/ml.}$ | $<1 \times 10^{-1/ml.}$ | $\geq 10^{4.3}$ log 10 |
| Test II | Herpesvirus Type I | $1 \times 10^{-4.3/ml.}$ | $<1 \times 10^{-1/ml.}$ | $<1 \times 10^{-1/ml.}$ | $\geq 10^{4.3}$ log 10 |

EXAMPLE IV 15 parts didecyl dimethyl ammonium chloride (50%), 10 parts n-alkyl (C14 50%, C12 40%, C16 10%) dimethyl benzyl ammonium chloride (50%), 5 parts linear primary ethoxylated alcohol, 4.33 parts tetrasodium ethylenediamine tetraacetate (38%), and 65.67 parts water were all mixed together. The resulting mixture was then diluted with water to include 488 p.p.m. n-alkyl (C14 50%, C12 40%, C16 10%) dimethyl benzyl ammonium chloride and didecyl dimethyl ammonium chloride combined. All tests were conducted in the presence of 5% weight blood serum and 400 p.p.m. hard water calculated as calcium carbonate.

The bacteriological activity of the above formulation was illustrated by conducting Use-Dilution Confirmation Tests, modified, in accordance with the A.O.A.C. Manual, 12th Edition, 1975 pages 56-60. The following results were noted:

| | No. of Carriers | No. of Positives |
|---|---|---|
| Gram-Negative Organisms | | |
| Pseudomonas aeruginosa | 90 | 0 |
| Salmonella choleraesuis | 90 | 0 |
| Enterobacter cloacae | 20 | 0 |
| Klebsiella pneumoniae | 20 | 0 |
| Proteus mirabilis | 20 | 0 |
| Shigella flexneri | 20 | 0 |
| Enterobacter | 20 | 0 |

-continued

| | No. of Carriers | No. of Positives |
|---|---|---|
| *Escherichia coli* | 20 | 0 |
| *Serratia marcescens* | 20 | 0 |
| *Proteus vulgaris* | 20 | 0 |
| *Shigella sonnei* | 20 | 0 |
| Gram-Positive Organisms | | |
| *Staphylococus aureus* | 180 | 0 |
| *Staphylococcus aureus* phage 80 | 20 | 0 |
| *Staphylococcus aureus* phage 81 | 20 | 0 |
| *Streptococcus pyogenes* | 20 | 0 |
| *Staphylococcus epidermidis* | 20 | 0 |

The fungicidal activity of the formulation was demonstrated according to the A.O.A.C. Fungicidal Test, modified, against Trychophyton Interdigitale. See A.O.A.C. Fungicidal Test, 12th Edition, 1975, page 63. The following results were noted:

| | 5 Minutes | | 10 Minutes | | 15 Minutes | |
|---|---|---|---|---|---|---|
| | Prim. | Second. | Prim. | Second. | Prim. | Second. |
| Test I | — | — | — | — | — | — |
| Test II | — | — | — | — | — | — |

The formulation's activity as a viricide was also demonstrated according to viricidal carriers method, modified, accepted by the Environmental Protection Agency against Adeno Virus Type III, Vaccinia, Influenza A/Texas, Herpes Virus Type I. The following results were noted:

| | VIRUS: | $TCID_{50}$ | $TCLD_{50}$ | $TCTD_{50}$ | $TCID_{50} - TCLD_{50} =$ |
|---|---|---|---|---|---|
| Test I | Adenovirus Type III | $1 \times 10^{-4.5/ml}$ | $<1 \times 10^{-1/ml}$ | $<1 \times 10^{-1/ml}$ | $\geq 10^{4.5}$ log 10 |
| Test II | Adenovirus Type III | $1 \times 10^{-4.5/ml}$ | $<1 \times 10^{-1/ml}$ | $<1 \times 10^{-1/ml}$ | $\geq 10^{4.5}$ log 10 |
| Test I | Vaccinia | $1 \times 10^{-5.5/ml}$ | $<1 \times 10^{-1/ml}$ | $<1 \times 10^{-1/ml}$ | $\geq 10^{5.5}$ log 10 |
| Test II | Vaccinia | $1 \times 10^{-5.5/ml}$ | $<1 \times 10^{-1/ml}$ | $<1 \times 10^{-1/ml}$ | $\geq 10^{5.5}$ log 10 |
| Test I | Influenza A/Texas | $1 \times 10^{-4.5/ml}$ | $<1 \times 10^{-1/ml}$ | $<1 \times 10^{-1/ml}$ | $\geq 10^{4.5}$ log 10 |
| Test II | Influenza A/Texas | $1 \times 10^{-4.5/ml}$ | $<1 \times 10^{-1/ml}$ | $<1 \times 10^{-1/ml}$ | $\geq 10^{4.5}$ log 10 |
| Test I | Herpesvirus Type I | $1 \times 10^{-4.3/ml}$ | $<1 \times 10^{-1/ml}$ | $<1 \times 10^{-1/ml}$ | $\geq 10^{4.3}$ log 10 |
| Test II | Herpesvirus Type I | $1 \times 10^{-4.3/ml}$ | $<1 \times 10^{-1/ml}$ | $<1 \times 10^{-1/ml}$ | $\geq 10^{4.3}$ log 10 |

EXAMPLE V 15 parts didecyl dimethyl ammonium chloride (50%), 10 parts n-alkyl (C14 50%, C12 40%, C16 10%) dimethyl benzyl ammonium chloride (50%), 5 parts linear primary ethoxylated alcohol, 4.33 parts tetrasodium ethylenediamine tetraacetate (38%), and 65.67 parts water were all mixed together. The resulting mixture was then diluted with distilled water to include 600 p.p.m. n-alkyl (C14 50%, C12 40%, C16 10%) dimethyl benzyl ammonium chloride and didecyl dimethyl ammonium chloride combined.

The bacteriological activity of the above formulation was illustrated by conducting Use-Dilution Confirmation Tests in accordance with the A.O.A.C. Manual, 12th Edition, 1975 pages 56-60. The following results were noted:

| | No. of Carriers | No. of Positives |
|---|---|---|
| Gram-Negative Organisms | | |
| *Pseudomonas aeruginosa* | 90 | 0 |
| *Salmonella choleraesuis* | 90 | 0 |
| *Enterobacter cloacae* | 20 | 0 |
| *Klebsiella pneumoniae* | 20 | 0 |
| *Proteus mirabilis* | 20 | 0 |
| *Shigella flexneri* | 20 | 0 |
| *Enterobacter aerogenes* | 20 | 0 |
| *Escherichia coli* | 20 | 0 |
| *Serratia marcescens* | 20 | 0 |
| *Proteus vulgaris* | 20 | 0 |
| *Shigella sonnei* | 20 | 0 |
| Gram-Positive Organisms | | |
| *Staphylococcus aureus* | 180 | 0 |
| *Staphylococcus aureus* phage 80 | 60 | 0 |
| *Staphylococcus aureus* phage 81 | 60 | 0 |
| *Streptococcus pyogenes* | 20 | 0 |
| *Staphylococcus epidermidis* | 20 | 0 |

The fungicidal activity of the formulation was demonstrated according to the A.O.A.C. Fungicidal Test against Trychophyton interdigitale. See A.O.A.C. Fungicidal Test, 12th Edition, 1975, page 63. The following results were noted:

| | 5 Minutes | | 10 Minutes | | 15 Minutes | |
|---|---|---|---|---|---|---|
| | Prim. | Second. | Prim. | Second. | Prim. | Second. |
| Test I | — | — | — | — | — | — |
| Test II | — | — | — | — | — | — |

The formulation's activity as a viricide was also demonstrated according to viricidal carriers method accepted by the Environmental Protection Agency against Adenovirus Type III, Vaccinia, Influenza A/Texas, Herpes Virus Type I. The following results were noted:

| | VIRUS: | $TCID_{50}$ | $TCLD_{50}$ | $TCTD_{50}$ | $TCID_{50} - TCLD_{50} =$ |
|---|---|---|---|---|---|
| Test I | Adenovirus Type III | $1 \times 10^{-4.5/ml}$ | $<1 \times 10^{-1/ml}$ | $<1 \times 10^{-1/ml}$ | $\geq 10^{4.5}$ log 10 |
| Test II | Adenovirus Type III | $1 \times 10^{-4.5/ml}$ | $<1 \times 10^{-1/ml}$ | $<1 \times 10^{-1/ml}$ | $\geq 10^{4.5}$ log 10 |
| Test I | Vaccinia | $1 \times 10^{-5.5/ml}$ | $<1 \times 10^{-1/ml}$ | $<1 \times 10^{-1/ml}$ | $\geq 10^{5.5}$ log 10 |
| Test II | Vaccinia | $1 \times 10^{-5.5/ml}$ | $<1 \times 10^{-1/ml}$ | $<1 \times 10^{-1/ml}$ | $\geq 10^{5.5}$ log 10 |
| Test I | Influenza A/Texas | $1 \times 10^{-4.5/ml}$ | $<1 \times 10^{-1/ml}$ | $<1 \times 10^{-1/ml}$ | $\geq 10^{4.5}$ log 10 |
| Test II | Influenza A/Texas | $1 \times 10^{-4.5/ml}$ | $<1 \times 10^{-1/ml}$ | $<1 \times 10^{-1/ml}$ | $\geq 10^{4.5}$ log 10 |
| Test I | Herpesvirus Type I | $1 \times 10^{-4.3/ml}$ | $<1 \times 10^{-1/ml}$ | $<1 \times 10^{-1/ml}$ | $\geq 10^{4.3}$ log 10 |
| Test II | Herpesvirus Type I | $1 \times 10^{-4.3/ml}$ | $<1 \times 10^{-1/ml}$ | $<1 \times 10^{-1/ml}$ | $\geq 10^{4.3}$ log 10 |

EXAMPLE VI 15 parts didecyl dimethyl ammonium chloride (50%), 10 parts n-alkyl (C14 50%, C12 40%, C16 10%) dimethyl benzyl ammonium chloride (50%), 5 parts linear primary ethoxylated alcohol, 4.33 parts tetrasodium ethylenediamine tetraacetate (38%), and 65.67 parts water were all mixed together. The resulting mixture was then diluted with water to include 600 p.p.m. n-alkyl (C14 50%, C12 40%, C16 10%) dimethyl benzyl ammonium chloride and didecyl dimethyl ammonium chloride combined. All water was hard water containing approximately 1000 p.p.m. calculated as calcium carbonate.

The bacteriological activity of the above formulation was illustrated by conducting Use-Dilution Confirmation Tests, modified, in accordance with the A.O.A.C. Manual, 12th Edition, 1975 pages 56-60. The following results were noted:

| Gram-Negative Organisms | No. of Carriers | No. Positives |
|---|---|---|
| Pseudomonas aeruginosa | 90 | 0 |
| Salmonella choleraesuis | 90 | 0 |
| Enterobacter cloacae | 20 | 0 |
| Klebsiella peumoniae | 20 | 0 |
| Proteus mirabilis | 20 | 0 |
| Shigella flexneri | 20 | 0 |
| Enterobacter aerogenes | 20 | 0 |
| Escherichia coli | 20 | 0 |
| Serratia marcescens | 20 | 0 |
| Proteus vulgaris | 20 | 0 |
| Shigella sonnei | 20 | 0 |

The fungicidal activity of the formulation was demonstrated according to the A.O.A.C. Fungicidal Test, modified, against Trychophyton interdigitale. See A.O.A.C. Fungicidal Test, 12th Edition, 1975, page 63. The following results were noted:

|  | 5 Minutes | | 10 Minutes | | 15 Minutes | |
|---|---|---|---|---|---|---|
|  | Prim. | Second. | Prim. | Second. | Prim. | Second. |
| Test I | — | — | — | — | — | — |
| Test II | — | — | — | — | — | — |

The formulation's activity as a viricide was also demonstrated according to viricidal carriers method, modified, accepted by the Environmental Protection Agency against Adenovirus Type III, Vaccinia, Influenza A/Texas, Herpes Virus Type I. The following results were noted:

15 parts didecyl dimethyl ammonium chloride (50%), 10 parts n-alkyl (C14 50%, C12 40%, C16 10%) dimethyl benzyl ammonium chloride (50%), 5 parts linear primary ethoxylated alcohol, 4.33 parts tetrasodium ethylenediamine tetraacetate (38%), and 65.67 parts water were all mixed together. The resulting mixture was then diluted with distilled water to include 600 p.p.m. n-alkyl (C14 50%, C12 40%, C16 10%) dimethyl benzyl ammonium chloride and didecyl dimethyl ammonium chloride combined. All tests were conducted in the presence of 5% weight blood serum.

The bacteriological activity of the above formulation was illustrated by conducting Use-Dilution Confirmation Tests, modified, in accordance with the A.O.A.C. Manual, 12th Edition, 1975 pages 56-60. The following results were noted:

|  | No. of Carriers | No. of Positives |
|---|---|---|
| Gram-Negative Organisms | | |
| Pseudomonas aeruginosa | 90 | 0 |
| Salmonella choleraesuis | 90 | 0 |
| Enterobacter cloacae | 20 | 0 |
| Klebsiella pneumoniae | 20 | 0 |
| Proteus mirabilis | 20 | 0 |
| Shigella flexneri | 20 | 0 |
| Enterobacter aerogenes | 20 | 0 |
| Escherichia coli | 20 | 0 |
| Serratia marcescens | 20 | 0 |
| Proteus vulgaris | 20 | 0 |
| Shigella sonnei | 20 | 0 |
| Gram-Positive Organisms | | |
| Staphylococcus aureus | 180 | 0 |
| Staphylococcus aureus phage 80 | 60 | 0 |
| Staphylococcus aureus phage 81 | 60 | 0 |
| Streptococcus pyogenes | 20 | 0 |
| Staphylococcus epidermidis | 20 | 0 |

The fungicidal activity of the formulation was demonstrated according to the A.O.A.C. Fungicidal Test, modified, against Trychophyton interdigitale. See A.O.A.C. Fungicidal Test, 12th Edition, 1975, page 63. The following results were noted:

|  | 5 Minutes | | 10 Minutes | | 15 Minutes | |
|---|---|---|---|---|---|---|
|  | Prim. | Second. | Prim. | Second. | Prim. | Second. |
| Test I | — | — | — | — | — | — |
| Test II | — | — | — | — | — | — |

The formulation's activity as a viricide was also demonstrated according to viricidal carriers method, modified, accepted by the Environmental Protection Agency against Adenovirus Type III, Vaccinia, Influenza A/Texas, Herpes Virus Type I. The following results were noted:

| | VIRUS: | $TCID_{50}$ | $TCLD_{50}$ | $TCTD_{50}$ | $TCID_{50} - TCLD_{50} =$ |
|---|---|---|---|---|---|
| Test I | Adenovirus Type III | $1 \times 10^{-4.5/ml}$ | $<1 \times 10^{-1/ml}$ | $<1 \times 10^{-1/ml}$ | $\geq 10^{4.5} \log 10$ |
| Test II | Adenovirus Type III | $1 \times 10^{-4.5/ml}$ | $<1 \times 10^{-1/ml}$ | $<1 \times 10^{-1/ml}$ | $\geq 10^{4.5} \log 10$ |
| Test I | Vaccinia | $1 \times 10^{-5.5/ml}$ | $<1 \times 10^{-1/ml}$ | $<1 \times 10^{-1/ml}$ | $\geq 10^{5.5} \log 10$ |
| Test II | Vaccinia | $1 \times 10^{-5.5/ml}$ | $<1 \times 10^{-1/ml}$ | $<1 \times 10^{-1/ml}$ | $\geq 10^{5.5} \log 10$ |
| Test I | Influenza A/Texas | $1 \times 10^{-4.5/ml}$ | $<1 \times 10^{-1/ml}$ | $<1 \times 10^{-1/ml}$ | $\geq 10^{4.5} \log 10$ |
| Test II | Influenza A/Texas | $1 \times 10^{-4.5/ml}$ | $<1 \times 10^{-1/ml}$ | $<1 \times 10^{-1/ml}$ | $\geq 10^{4.5} \log 10$ |
| Test I | Herpesvirus Type I | $1 \times 10^{-4.3/ml}$ | $<1 \times 10^{-1/ml}$ | $<1 \times 10^{-1/ml}$ | $\geq 10^{4.3} \log 10$ |
| Test II | Herpesvirus Type I | $1 \times 10^{-4.3/ml}$ | $<1 \times 10^{-1/ml}$ | $<1 \times 10^{-1/ml}$ | $\geq 10^{4.3} \log 10$ |

EXAMPLE VII 15 parts didecyl dimethyl ammonium chloride (50%), 10 parts n-alkyl C14 50%, C12 40%, C16 10%) diresults were noted:

| VIRUS: | TCID$_{50}$ | TCLD$_{50}$ | TCTD$_{50}$ | TCID$_{50}$ − TCLD$_{50}$ = |
|---|---|---|---|---|
| Test I Adenovirus Type III | $1 \times 10^{-4.5/ml.}$ | $<1 \times 10^{-1/ml}$ | $<1 \times 10^{-1/ml.}$ | $\geq 10^{4.5}$ log 10 |
| Test II Adenovirus Type III | $1 \times 10^{-4.5/ml.}$ | $<1 \times 10^{-1/ml}$ | $<1 \times 10^{-1/ml.}$ | $\geq 10^{4.5}$ log 10 |
| Test I Vaccinia | $1 \times 10^{-5.5/ml.}$ | $<1 \times 10^{-1/ml.}$ | $<1 \times 10^{-1/ml.}$ | $\geq 10^{5.5}$ log 10 |
| Test II Vaccinia | $1 \times 10^{-5.5/ml.}$ | $<1 \times 10^{-1/ml.}$ | $<1 \times 10^{-1/ml.}$ | $\geq 10^{5.5}$ log 10 |
| Test I Influenza A/Texas | $1 \times 10^{-4.5/ml.}$ | $<1 \times 10^{-1/ml.}$ | $<1 \times 10^{-1/ml.}$ | $\geq 10^{4.5}$ log 10 |
| Test II Influenza A/Texas | $1 \times 10^{-4.5/ml.}$ | $<1 \times 10^{-1/ml.}$ | $<1 \times 10^{-1/ml.}$ | $\geq 10^{4.5}$ log 10 |
| Test I Herpesvirus Type I | $1 \times 10^{-4.3/ml.}$ | $<1 \times 10^{-1/ml.}$ | $<1 \times 10^{-1/ml.}$ | $\geq 10^{4.3}$ log 10 |
| Test II Herpesvirus Type I | $1 \times 10^{-4.3/ml.}$ | $<1 \times 10^{-1/ml.}$ | $<1 \times 10^{-1/ml.}$ | $\geq 10^{4.3}$ log 10 |

EXAMPLE VIII 15 parts didecyl dimethyl ammonium chloride (50%), 10 parts n-alkyl (C14 50%, C12 40%, C16 10%) dimethyl benzyl ammonium chloride (50%), 5 parts linear primary ethoxylated alcohol, 4.33 parts tetrasodium ethylenediamine tetraacetate (38%), and 65.67 parts water were all mixed together. The resulting mixture was then diluted with water to include 600 p.p.m. n-alkyl (C14 50%, C12 40%, C16 10%) dimethyl benzyl ammonium chloride and didecyl dimethyl ammonium chloride combined. All tests were conducted in the presence of 5% weight blood serum and 400 p.p.m. hard water calculated as calcium carbonate.

The bacteriological activity of the above formulation was illustrated by conducting Use-Dilution Confirmation Tests, modified, in accordance with the A.O.A.C. Manual, 12th Edition, 1975 pages 56–60. The following results were noted:

|  | No. of Carriers | No. of Positives |
|---|---|---|
| Gram-Negative Organisms |  |  |
| Pseudomonas aeruginosa | 90 | 0 |
| Salmonella choleraesuis | 90 | 0 |
| Enterobacter cloacae | 20 | 0 |
| Klebsiella pneumoniae | 20 | 0 |
| Proteus mirabilis | 20 | 0 |
| Shigella flexneri | 20 | 0 |
| Enterobacter aerogenes | 20 | 0 |
| Escherichia coli | 20 | 0 |
| Serratia marcescens | 20 | 0 |
| Proteus vulgaris | 20 | 0 |
| Shigella sonnei | 20 | 0 |
| Gram-Positive Organisms |  |  |
| Staphylococcus aureus | 180 | 0 |
| Staphylococcus aureus phage 80 | 60 | 0 |
| Staphylococcus aureus phage 81 | 60 | 0 |
| Streptococcus pyogenes | 20 | 0 |
| Staphylococcus epidermidis | 20 | 0 |

The fungicidal activity of the formulation was demonstrated according to the A.O.A.C. Fungicidal Test, modified, against Trychophyton interdigitale. See A.O.A.C. Fungicidal Test, 12th Edition, 1975, page 63. The following results were noted:

|  | 5 Minutes | | 10 Minutes | | 15 Minutes | |
|---|---|---|---|---|---|---|
|  | Prim. | Second. | Prim. | Second. | Prim. | Second. |
| Test I | — | — | — | — | — | — |
| Test II | — | — | — | — | — | — |

The formulation's activity as a viricide was also demonstrated according to viricidal carriers method, modified, accepted by the Environmental Protection Agency against Adenovirus Type III, Vaccinia, Influenza A/Texas, Herpes Virus Type I. The following results were noted:

| VIRUS: | TCID$_{50}$ | TCLD$_{50}$ | TCTD$_{50}$ | TCID$_{50}$ − TCLD$_{50}$ = |
|---|---|---|---|---|
| Test I Adenovirus Type III | $1 \times 10^{-4.5/ml.}$ | $<1 \times 10^{-1/ml}$ | $<1 \times 10^{-1/ml.}$ | $\geq 10^{4.5}$ log 10 |
| Test II Adenovirus Type III | $1 \times 10^{-4.5/ml.}$ | $<1 \times 10^{-1/ml}$ | $<1 \times 10^{-1/ml.}$ | $\geq 10^{4.5}$ log 10 |
| Test I Vaccinia | $1 \times 10^{-5.5/ml.}$ | $<1 \times 10^{-1/ml.}$ | $<1 \times 10^{-1/ml.}$ | $\geq 10^{5.5}$ log 10 |
| Test II Vaccinia | $1 \times 10^{-5.5/ml.}$ | $<1 \times 10^{-1/ml.}$ | $<1 \times 10^{-1/ml.}$ | $\geq 10^{5.5}$ log 10 |
| Test I Influenza A/Texas | $1 \times 10^{-4.5/ml.}$ | $<1 \times 10^{-1/ml.}$ | $<1 \times 10^{-1/ml.}$ | $\geq 10^{4.5}$ log 10 |
| Test II Influenza A/Texas | $1 \times 10^{-4.5/ml.}$ | $<1 \times 10^{-1/ml.}$ | $<1 \times 10^{-1/ml.}$ | $\geq 10^{4.5}$ log 10 |
| Test I Herpesvirus Type I | $1 \times 10^{-4.3/ml.}$ | $<1 \times 10^{-1/ml.}$ | $<1 \times 10^{-1/ml.}$ | $\geq 10^{4.3}$ log 10 |
| Test II Herpesvirus Type I | $1 \times 10^{-4.3/ml.}$ | $<1 \times 10^{-1/ml.}$ | $<1 \times 10^{-1/ml.}$ | $\geq 10^{4.3}$ log 10 |

EXAMPLE IX 30 parts didecyl dimethyl ammonium chloride (50%), 20 parts n-alkyl (C14 50%, C12 40%, C16 10%) dimethyl benzyl ammonium chloride and 50 parts water were all mixed together. The resulting mixture was then diluted with water to include 150 p.p.m. n-alkyl (C14 50%, C12 40%, C16 10%) dimethyl benzyl ammonium chloride and didecyl dimethyl ammonium chloride combined. All water was hard water containing approximately 800 p.p.m. calculated as calcium carbonate.

The germicidal and detergent sanitizer activity of the above formulation was illustrated by conducting A.O.A.C. Germicidal and Detergent Sanitizer tests, modified in accordance with the A.O.A.C. Manual, 13th Edition, 1980. The following results were noted:

|  | Organism | Activity (%) | Quat Conc. PPM | Hard Water PPM | No. Survivors-% Kill 30 Sec. | | 60 Sec. | |
|---|---|---|---|---|---|---|---|---|
|  |  |  |  |  | # | % | # | % |
| Test I | Staphylococcus aureus | 50 | 150 | 800 | 780 | 99.999 | 15 | 99.999 |

-continued

|  | Organism | Activity (%) | Quat Conc. PPM | Hard Water PPM | No. Survivors-% Kill | | | |
|---|---|---|---|---|---|---|---|---|
|  |  |  |  |  | 30 Sec. | | 60 Sec. | |
|  |  |  |  |  | # | % | # | % |
| Test II | Staphylococcus Aureus | 50 | 150 | 800 | 625 | 99.999 | 5 | 99.999 |
| Test III | Staphylococcus Aureus | 50 | 150 | 800 | 485 | 99.999 | 35 | 99.999 |
| Test I | Escherichia coli | 50 | 150 | 800 | 545 | 99.999 | 65 | 99.999 |
| Test II | Escherichia coli | 50 | 150 | 800 | 790 | 99.999 | 40 | 99.999 |
| Test III | Escherichia coli | 50 | 150 | 800 | 835 | 99.999 | 20 | 99.999 |

EXAMPLE X 30 parts didecyl dimethyl ammonium chloride (50%), 20 parts n-alkyl (C14 50%, C12 40%, C16 10%) dimethyl benzyl ammonium chloride and 50 parts water were all mixed together. The resulting mixture was then diluted with distilled water to include 150 p.p.m. n-alkyl (C14 50%, C12 40%, C16 10%) dimethyl benzyl ammonium chloride and didecyl dimethyl ammonium chloride combined.

The germicidal and detergent sanitizer activity of the above formulation was illustrated by conducting A.O.A.C. Germicidal and Detergent Sanitizer Tests in accordance with the A.O.A.C. Manual, 13th Edition, 1980. The following results were noted:

|  | Organism | Activity (%) | Quat Conc. PPM | No. Survivors-% Kill | | | |
|---|---|---|---|---|---|---|---|
|  |  |  |  | 30 Sec. | | 60 Sec. | |
|  |  |  |  | # | % | # | % |
| Test I | Staphylococcus aureus | 50 | 150 | 780 | 99.999 | 15 | 99.999 |
| Test II | Staphylococcus Aureus | 50 | 150 | 625 | 99.999 | 5 | 99.999 |
| Test III | Staphylococcus Aureus | 50 | 150 | 485 | 99.999 | 35 | 99.999 |
| Test I | Escherichia coli | 50 | 150 | 545 | 99.999 | 65 | 99.999 |
| Test II | Escherichia coli | 50 | 150 | 790 | 99.999 | 40 | 99.999 |
| Test III | Escherichia coli | 50 | 150 | 835 | 99.999 | 20 | 99.999 |

EXAMPLE XI 30 parts didecyl dimethyl ammonium chloride (50%), 20 parts n-alkyl (C14 50%, C12 40%, C16 10%) dimethyl benzyl ammonium chloride (50%), and 50 parts water were all mixed together. The resulting mixture was then diluted with water to include 300 p.p.m. n-alkyl (C14 50%, C12 40%, C16 10%) dimethyl benzyl ammonium chloride and didecyl dimethyl ammonium chloride combined. All water was hard water containing approximately 800 p.p.m. calculated as calcium carbonate.

The germicidal and detergent sanitizer activity of the above formulation was illustrated by conducting A.O.A.C. Germicidal and Detergent Sanitizer Tests, modified, in accordance with the A.O.A.C. Manual, 13th Edition, 1980. The following results were noted:

|  | Organism | Activity (%) | Quat Conc. PPM | Hard Water PPM | No. Survivors-% Kill | | | |
|---|---|---|---|---|---|---|---|---|
|  |  |  |  |  | 30 Sec. | | 60 Sec. | |
|  |  |  |  |  | # | % | # | % |
| Test I | Staphylococcus aureus | 50 | 150 | 800 | 780 | 99.999 | 15 | 99.999 |
| Test II | Staphylococcus Aureus | 50 | 150 | 800 | 625 | 99.999 | 5 | 99.999 |
| Test III | Staphylococcus Aureus | 50 | 150 | 800 | 485 | 99.999 | 35 | 99.999 |
| Test I | Escherichia coli | 50 | 150 | 800 | 545 | 99.999 | 65 | 99.999 |
| Test II | Escherichia coli | 50 | 150 | 800 | 790 | 99.999 | 40 | 99.999 |
| Test III | Escherichia coli | 50 | 150 | 800 | 835 | 99.999 | 20 | 99.999 |

EXAMPLE XII 30 parts didecyl dimethyl ammonium chloride (50%), 20 parts n-alkyl (C14 50%, C12 40%, C16 10%) dimethyl benzyl ammonium chloride (50%), and 50 parts water were all mixed together. The resulting mixture was then diluted with distilled water to include 300 p.p.m. n-alkyl C14 50%, C12 40%, C16 10%) dimethyl benzyl ammonium chloride and didecyl dimethyl ammonium chloride combined.

The germicidal and detergent sanitizer activity of the above formulation was illustrated by conducting A.O.A.C. Germicidal and Detergent Sanitizer Tests in accordance with the A.O.A.C. Manual, 13th Edition, 1980. The following results were noted:

|  | Organism | Activity (%) | Quat Conc. PPM | No. Survivors-% Kill | | | |
|---|---|---|---|---|---|---|---|
|  |  |  |  | 30 Sec. | | 60 Sec. | |
|  |  |  |  | # | % | # | % |
| Test I | Staphylococcus aureus | 50 | 150 | 780 | 99.999 | 15 | 99.999 |
| Test II | Staphylococcus Aureus | 50 | 150 | 625 | 99.999 | 5 | 99.999 |
| Test III | Staphylococcus Aureus | 50 | 150 | 485 | 99.999 | 35 | 99.999 |
| Test I | Escherichia coli | 50 | 150 | 545 | 99.999 | 65 | 99.999 |
| Test II | Escherichia coli | 50 | 150 | 790 | 99.999 | 40 | 99.999 |
| Test III | Escherichia coli | 50 | 150 | 835 | 99.999 | 20 | 99.999 |

EXAMPLE XIII 15 parts didecyl dimethyl ammonium chloride (50%), 10 parts n-alkyl (C14 50%, C12 40%, C16 10%) dimethyl benzyl ammonium chloride (50%), 5 parts linear primary ethoxylated alcohol, 4.33 parts tetrasodium ethylenediamine tetraacetate (38%), and 65.67 parts water were all mixed together. The resulting mixture was then diluted with water to include 150 p.p.m. n-alkyl (C14 50%, C12 40%, C16 10%) dimethyl benzyl ammonium chloride and didecyl dimethyl ammonium chloride combined. All water was hard water containing approximately 400 p.p.m. calculated as calcium carbonate and 5% organic serum, simultaneously.

The germicidal and detergent sanitizer activity of the above formulation was illustrated by conducting A.O.A.C. Germicidal and Detergent Sanitizer Tests, modified, in accordance with the A.O.A.C. Manual, 13th Edition, 1980. The following results were noted:

|  | Organism | Quat Conc. PPM | Hard Water PPM | No. Survivors-% Kill | | | |
|---|---|---|---|---|---|---|---|
|  |  |  |  | 30 Sec. | | 60 Sec. | |
|  |  |  |  | # | % | # | % |
| Test I | Staphylococcus aureus | 150 | 400 | 960 | 99.999 | 120 | 99.999 |
| Test II | Staphylococcus Aureus | 150 | 400 | 1010 | 99.999 | 105 | 99.999 |
| Test III | Staphylococcus Aureus | 150 | 400 | 1100 | 99.999 | 135 | 99.999 |
| Test I | Escherichia coli | 150 | 400 | 1080 | 99.999 | 165 | 99.999 |
| Test II | Escherichia coli | 150 | 400 | 1250 | 99.999 | 135 | 99.999 |
| Test III | Escherichia coli | 150 | 400 | 1225 | 99.999 | 125 | 99.999 |

EXAMPLE XIV 15 parts didecyl dimethyl ammonium chloride (50%), 10 parts n-alkyl (C14 50%, C12 40%, C16 10%) dimethyl benzyl ammonium chloride (50%), 5 parts linear primary ethoxylated alcohol, 4.33 parts tetrasodium ethylenediamine tetraacetate (38%), and 65.67 parts water were all mixed together. The resulting mixture was then diluted with water to include 300 p.p.m. n-alkyl (C14 50%, C12 40%, C16 10%) dimethyl benzyl ammonium chloride and didecyl dimethyl ammonium chloride combined. All water was hard water containing approximately 400 p.p.m. calculated as calcium carbonate and 5% organic serum, simultaneously.

The germicidal and detergent sanitizer activity of the above formulation was illustrated by conducting A.O.A.C. Germicidal and Detergent Sanitizer Tests, modified, in accordance with the A.O.A.C. Manual, 13th Edition, 1980. The following results were noted:

|  | Organism | Quat Conc. PPM | Hard Water PPM | No. Survivors-% Kill | | | |
|---|---|---|---|---|---|---|---|
|  |  |  |  | 30 Sec. | | 60 Sec. | |
|  |  |  |  | # | % | # | % |
| Test I | Staphylococcus aureus | 150 | 400 | 960 | 99.999 | 120 | 99.999 |
| Test II | Staphylococcus Aureus | 150 | 400 | 1010 | 99.999 | 105 | 99.999 |
| Test III | Staphylococcus Aureus | 150 | 400 | 1100 | 99.999 | 135 | 99.999 |
| Test I | Escherichia coli | 150 | 400 | 1080 | 99.999 | 165 | 99.999 |
| Test II | Escherichia coli | 150 | 400 | 1250 | 99.999 | 135 | 99.999 |
| Test III | Escherichia coli | 150 | 400 | 1225 | 99.999 | 125 | 99.999 |

Thus, by the invention, an improved germicidal composition has been provided. The germicidal composition of the invention can be diluted and utilized as an improved disinfectant and/or sanitizer. The germicidal composition can also be utilized as a fungicide or a viricide. Further, the improved germicidal composition is a disinfectant, fungicide and/or viricide in dilutions of distilled water, hard water, in the presence of 5% organic soil, and hard water plus in the presence of 5% organic soil simultaneously.

While there have been described above the principles of this invention in connection with specific formulations, it is to be clearly understood that this description is made only by way of example and not as a limitation to the scope of the invention.

What is claimed is:

1. A germicide composition both germicidally active in hard water and germicidially active in the presence of up to about 5% organic soil when present in an amount of at least 300 ppm in an aqueous solution, comprising a blend of didecyl dimethyl ammonium chloride and n-alkyl (C14 50%, C12 40%, C16 10%) dimethyl benzyl ammonium chloride, said didecyl dimethyl ammonium chloride and n-alkyl (C14 50%, C12 40%, C16 10%) dimethyl benzyl ammonium chloride being present in about a 60/40 weight ratio.

2. The composition of claim 2 further comprising a nonionic detergent.

3. The composition of claim 2 further comprising a detergent builder.

4. The active ingredients of an aqueous germicidal composition consisting of a blend of didecyl dimethyl ammonium chloride and n-alkyl (C14 50%, C12 40%, C16 10%) dimethyl benzyl ammonium chloride in about a 60/40 by weight ratio.

5. An aqueous solution of a germicidal composition comprising hard water and a germicidally effective amount of a composition consisting of essentially a blend of didecyl dimethyl ammonium chloride and n-alkyl (C14 50%, C12 40%, C16 10%) dimethyl benzyl ammonium chloride in the presence of up to about 5% organic soil, said didecyl dimethyl ammonium chloride and n-alkyl (C14 50%, C12 40%, C16 10%) dimethyl benzyl ammonium chloride being present in about a 60/40 by weight ratio.

6. The solution of claim 7 further comprising added ingredients chosen from the group consisting of nonionic detergents and combinations of nonionic detergents and detergent builders.

7. An aqueous solution of a germicidal composition comprising hard water and a germicidally effective amount of a composition consisting of essentially a blend of didecyl dimethyl ammonium chloride and n- alkyl (C14 50%, C12 40%, C16 10%) dimethyl benzyl ammonium chloride, said didecyl dimethyl ammonium chloride and n-alkyl (C14 50%, C12 40%, C16 10%) dimethyl benzyl ammonium chloride being present in about a 60/40 by weight ratio.

8. The solution of claim 7 further comprising added ingredients chosen from the group consisting of nonionic detergents and detergent builders and combinations thereof.

9. An aqueous germicidal solution wherein there is present a germicidally effective amount of a composition consisting of essentially a blend of didecyl dimethyl ammonium chloride and n-alkyl (C14 50%, C12 40%, C16 10%) dimethyl benzyl ammonium chloride, said didecyl dimethyl ammonium chloride and n-alkyl (C14 50%, C12 40%, C16 10%) dimethyl benzyl ammonium chloride being present in about a 60/40 by weight ratio.

10. The solution of claim 9 further comprising added ingredients chosen from the group consisting of nonionic detergents and detergent builders and combinations thereof.

11. A method of killing germs comprising contacting germs with an aqueous solution of from about 50 to about 3000 p.p.m. of a blend of didecyl dimethyl ammonium chloride and n-alkyl (C14 50%, C12 40%, C16 10%) dimethyl benzyl ammonium chloride, said didecyl dimethyl ammonium chloride and n-alkyl (C14 50%, C12 40%, C16 10%) dimethyl benzyl ammonium chloride being present in about a 60/40 by weight ratio.

12. The method of claim 11 wherein the water is hard water.

13. The method of claim 11 wherein the water is hard water in the presence of up to about 5% weight organic soil.

14. The method of claim 11 wherein said germs include germs chosen from the group consisting of Staphylococcus aureus, and Escherichia coli.

15. A method of killing germs comprising contacting germs with an aqueous of solution of from about 300 to about 3000 p.p.m. of a blend of didecyl dimethyl ammonium chloride and n-alkyl (C14 50%, C12 40%, C16 10%) dimethyl benzyl ammonium chloride, said didecyl dimethyl ammonium chloride and n-alkyl (C14 50%, C12 40%, C16 10%) dimethyl benzyl ammonium chloride being present in about a 60/40 by weight ratio.

16. The method of claim 15 wherein the water is hard water.

17. The method of claim 15 wherein the water is hard water containing up to about 5% weight organic soil.

18. The method of claim 15 wherein said germs include germs chosen from the group consisting of
Pseudomonas aeruginosa
Salmonella choleraesuis
Enterobacter cloacae
Klebsiella pneumoniae
Proteus mirabilis
Shigella flexneri
Enterobacter aerogenes
Escherichia coli
Serratia marcescens
Proteus vulgaris
Shigella sonnei
Staphylococcus aureus
Staphylococcus aureus phage 80
Staphylococcus aureus phage 81
Streptococcus pyogenes
Staphylococcus epidermidis
Trichophyton interdigitale
Herpes virus Type I
Adenovirus Type III
Influenza A/Texas, and
Vaccinia.

* * * * *